United States Patent
Andersen et al.

(10) Patent No.: US 6,808,532 B2
(45) Date of Patent: Oct. 26, 2004

(54) LASER TREATMENT FOR REDUCING WRINKLES

(76) Inventors: Dan E. Andersen, 755 Arnold Way, Menlo Park, CA (US) 94025; Eric F. Bernstein, 1321 Grenox Rd., Wynnewood, PA (US) 19096

( * ) Notice: Subject to any disclaimer, the term of this patent is extended or adjusted under 35 U.S.C. 154(b) by 0 days.

(21) Appl. No.: 09/738,523

(22) Filed: Dec. 15, 2000

(65) Prior Publication Data

US 2002/0077678 A1 Jun. 20, 2002

(51) Int. Cl.[7] .......................... A61N 5/06; A61N 5/067; A61B 18/20
(52) U.S. Cl. .......................................................... 607/89
(58) Field of Search .................. 606/2, 9; 607/88, 607/89; 128/898

(56) References Cited

U.S. PATENT DOCUMENTS

| | | | |
|---|---|---|---|
| 5,312,395 A | * 5/1994 | Tan et al. | 606/9 |
| 5,611,795 A | * 3/1997 | Slatkine | 606/9 |
| 5,807,386 A | * 9/1998 | Slatkine et al. | 606/9 |
| 5,810,801 A | * 9/1998 | Anderson et al. | 606/9 |
| 5,964,749 A | 10/1999 | Eckhouse et al. | 606/9 |
| 5,983,900 A | 11/1999 | Clement et al. | 128/898 |
| 6,045,548 A | 4/2000 | Furumoto et al. | 606/9 |
| 6,077,294 A | 6/2000 | Cho et al. | 607/89 |
| 6,110,195 A | * 8/2000 | Xie et al. | 607/89 |
| 6,210,426 B1 | * 4/2001 | Cho et al. | 607/89 |
| 6,273,884 B1 | * 8/2001 | Altshuler et al. | 606/9 |
| 6,312,450 B1 | * 11/2001 | Yavitz et al. | 607/88 |
| 6,387,089 B1 | * 5/2002 | Kreindel et al. | 606/9 |

OTHER PUBLICATIONS

T.S. Alster et al., "Improvement of facial acne scars by the 585 nm flashlamp–pumped pulsed dye laser," *Journal of the American Academy of Dermatology*, vol. 35, No. 1, Jul. 1996, pp. 79–81.

J.L. Cisneros et al., "The Q–switched Neodymium (Nd):YAG Laser with Quadruple Frequency," *Dermatol. Surg.*, vol. 24, 1998, pp. 345–350.

T.S. Alster et al., "Treatment of Scars: A Review," *Annuals of Plastic Surgery*, vol. 39, No. 4, Oct. 1997, pp. 418–432.

U.S. patent application No. 09/663,987, entitled "Method of Treating Hypotrophic Scars and Enlarged Pores," filed Sep. 18, 2000, pp. 1–16 and 3 pages of drawings.

* cited by examiner

*Primary Examiner*—George L. Walton
(74) *Attorney, Agent, or Firm*—Licata & Tyrrell P.C.

(57) ABSTRACT

Skin including wrinkles is irradiated with laser radiation having a wavelength between about 525 and 550 nanometers. The irradiation is delivered at a fluence that stimulates wound healing responses without actually inflicting a wound. This promotes deposition of dermal extracellular matrix. Absorption properties of hemoglobin and melanin in the 525 to 550 nanometer wavelength range provide that wound healing response is concentrated close to upper regions of the skin and accordingly close to the location of the wrinkles. The growth of dermal extracellular matrix "bulks-up" irradiated dermal tissue. This makes the depressions or folds of the wrinkles shallower and less apparent.

19 Claims, 2 Drawing Sheets ly to laser treatment
of dermatological imperfections. The invention relates in
particular to non-ablative laser treatment for reducing
wrinkles.

DISCUSSION OF BACKGROUND ART

Effective aesthetic treatment of wrinkles has hitherto
involved primarily the removal of tissue and subsequent
wound healing to improve their appearance. Chemical peels,
dermabrasion, and ablative laser skin resurfacing are used
routinely for this purpose. However, all of these methods
leave open wounds which must subsequently heal. There is
need for a laser treatment method for reducing wrinkles
which does not leave such open wounds.

SUMMARY OF THE INVENTION

The present invention is directed to a method for treating
wrinkles. In one aspect, the method of the present invention
comprises irradiating the skin to be treated with light
(electromagnetic radiation) having a wavelength selected
such that it is preferentially absorbed in a dermal region of
the skin including a melanocyte layer of the epidermis and
a region of superficial vasculature immediately below the
melanocyte layer. The light is delivered at a fluence sufficient that the preferential absorption thereof stimulates a
wound healing (regenerative) response in the dermal region
without causing a wound. The wound healing response
promotes growth of dermal extracellular matrix (ECM) in
the upper dermal region. The growth of dermal ECM
reduces the depth of the wrinkles.

Preferably, the light has a wavelength between about 525
and 550 nanometers (nm). The light may be delivered in the
form of pulses thereof or as a continuous beam swept or
scanned over an area of skin being treated.

In experimental treatments in accordance with the present
invention, pulsed electromagnetic radiation having a wavelength of 532 nm, delivered by a frequency-doubled
Nd:YAG laser was arranged to deliver a spot having a
diameter of about 3 millimeters (mm). The pulse duration
was about 2.0 milliseconds (ms). An average fluence of 5.5
Joules per square centimeter ($J/cm^2$) was used in repeated
treatments to treat eleven volunteer patients having facial
wrinkles. There was on average a 52% improvement in the
appearance of the wrinkles, as judged by the patients themselves.

BRIEF DESCRIPTION OF THE DRAWINGS

The accompanying drawings, which are incorporated in
and constitute a part of the specification, schematically
illustrate a preferred embodiment of the present invention,
and together with the general description given above and
the detailed description of the preferred embodiment given
below, serve to explain the principles of the invention.

DETAILED DESCRIPTION OF THE INVENTION

The method of the present invention relies on using laser
radiation to stimulate the skin's regenerative or wound
healing responses. The laser radiation wavelength and the
laser radiation fluence are selected such that the wound
healing responses are stimulated without actually inflicting
a wound. The wound healing responses promote growth or
production of dermal ECM. The term "wound" here is meant
to define an open wound, blister or any other effect which
would be manifest in, or lead to, a discontinuity in the
structure of tissue.

The biology of wound healing is a very complex process.
Cytokines released by the vascular endothelial cells and
epidermal keratinocytes are responsible for initiating the
increased production of ECM. These elements lie in the
uppermost regions of the skin. This ECM production process
takes place in a series of interrelated steps via the resident
cells of the dermis. By selecting a wavelength of laser
radiation in a range between about 525 and 550 nm, there is
an optimal stimulation of both keratinocytes and vascular
endothelial cells which causes the wound healing response
to be concentrated close to these upper regions of the skin,
and accordingly close to the location of imperfections being
treated.

The dermis is composed of cellular and extracellular
constituents that interact with one another to form a highly
ordered yet quite dynamic structure. Other than water, the
major components of the ECM are collagen, elastic fibers,
fibronectin, glycosaminoglycans, and proteoglycans. The
stimulated growth of dermal ECM "bulks-up" the dermal
tissue. This makes the depressions or "folds" of wrinkles
shallower and less apparent, if not eliminating them altogether.

The superficial vascular endothelium and the epidermal
keratinocytes are stimulated by heating them with light that
is well absorbed by components within both structures. This
requires that the light be optimally absorbed in both melanin
and in hemoglobin of the superficial vasculature.

Figure 1:
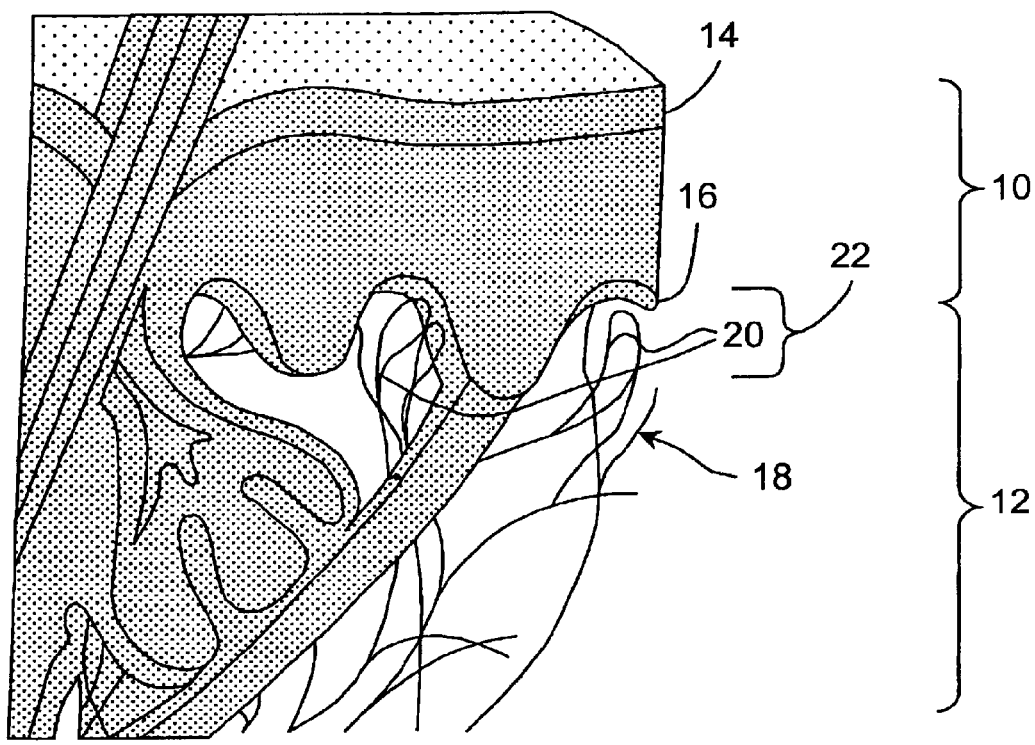
FIG. 1 schematically illustrates a section of human tissue
including layers and vasculature thereof.

FIG. 1 schematically illustrates a section of human skin
including a region 10 generally defined as the epidermis and
a region 12 generally defined as the dermis. The epidermis
10 includes an outer layer (stratum corneum) 14, and a lower
(melanocyte) layer 16 including melanin pigment. Some
keratinocytes are heavily pigmented and contain melanosomes which feed melanin to surrounding cells. These cells
are called melanocytes. The epidermis is made up primarily
of keratinocytes.

In the papillary or upper dermis 12, vasculature 18 has a
superficial portion thereof comprising a plurality of capillary
loops 20. In the method of the present invention, absorption
by melanin in melanocyte layer 16 and hemoglobin in
capillary loops 20 of vasculature 18 preferentially heats a
shallow region 20 immediately below layer 16, thereby
heating the layer by conduction and providing the desired
wound healing stimulus. It is believed, without being limited
to a particular theory, that heating of endothelial cells in the
walls of vessels of vasculature 18, in particular of the
capillary loops 20 close to the epidermis 10, induces the
secretion of cytokines that stimulate cells of the dermis 12
to produce the ECM.

Figure 2:
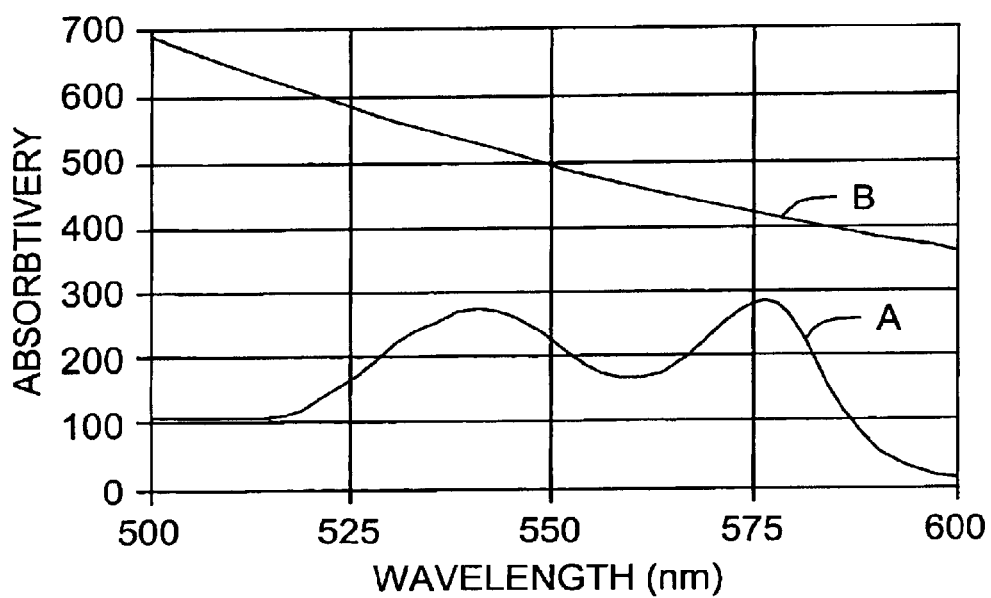
FIG. 2 is a graph schematically illustrating absorptivity of
hemoglobin and melanin as a function of wavelength in a
wavelength region of the visible electromagnetic spectrum
between 500 nanometers and 600 nanometers.

FIG. 2 graphically, schematically illustrates absorptivity
of blood (curve A) and melanin (curve B) as a function of
wavelength in a wavelength region between 500 nm and 600
nm in the visible electromagnetic spectrum. In the preferred
wavelength region of 525 to 550 nanometers absorptivity in hemoglobin is at or near a peak while absorption in melanin is also at a high level. The high melansome absorptivity helps in maintaining the desired heating effect at a superficial level in the skin being treated. By way of contrast, in the "yellow" wavelength region around 580 nm where dye lasers emit, melanosome absorptivity is significantly less than at 525 nm and approaches equality with hemoglobin absorptivity. This is one reason why dye lasers are preferred in prior-art treatment of vascular disorders and the like. In such treatments, absorption of radiation by melanin could cause undesirable side effects such as blistering of skin as well as preventing penetration of the radiation to the lower lying vasculature where it is needed.

In the inventive wrinkle treatment method, electromagnetic radiation (light) preferably having a wavelength between about 525 and 550 nm, and having an appropriate pulse duration and intensity, is used to provide a selective, localized temperature increase in the superficial vasculature 20 and, intentionally and therapeutically, in melanocyte layer 16. The temperature rise should be sufficient to stimulate the release of cytokines and other growth factors without appreciably damaging any of the structures of the skin. Preferably this temperature is less than about 70° C., but must of, course, be higher than normal body temperature. It is believed that at wavelengths increasingly shorter than 525 nm, as absorption becomes increasingly, proportionately higher in melanin than in hemoglobin, that sufficient heating of the target region can not be obtained without overheating the melanocyte layer and causing blistering. At wavelengths increasingly longer than 550 nm, decreasing melanin absorption will allow penetration of radiation to depths in the vasculature at which it is less therapeutically effective, if at all.

The treatment radiation is preferably delivered by a laser. One suitable laser for providing radiation in the inventive treatment of wrinkles is a frequency doubled Nd:YAG laser. Such a laser operates most efficiently by generating 1064 nm fundamental radiation and converting this radiation to 532 nm radiation by intracavity frequency doubling.

Figure 3:
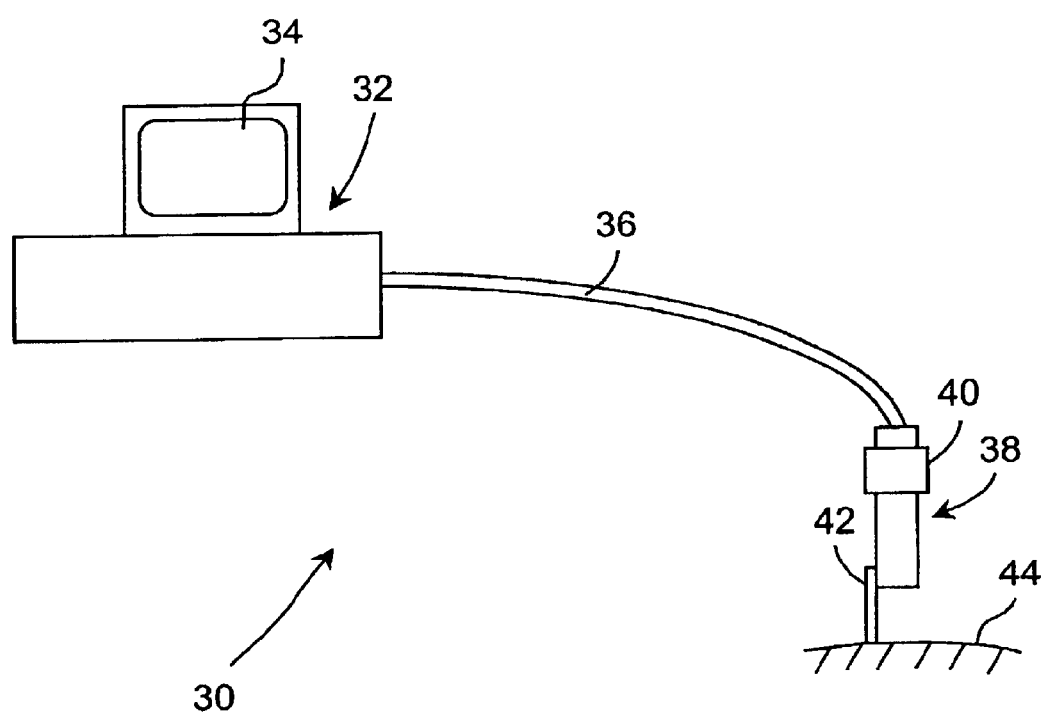
FIG. 3 schematically illustrates laser apparatus used for
experimental treatment of wrinkles in accordance with the
method of the present invention.

Referring now to FIG. 3, laser apparatus 30 used for experimental treatments in accordance with the present invention includes a Coherent® "VersaPulse V™" intracavity-frequency-doubled Nd:YAG laser 32 including a touch screen control display 34 for controlling operating parameters of the laser. Laser 32 delivers 532 nm radiation via a fiber-optic cable 36 to a handpiece 38. Handpiece 38 includes optics (not shown) which allow delivery of the 532 nm laser radiation focussed in a range of spot sizes. Spot sizes are selectively adjustable by rotating a control ring 40. A stand-off probe 42 attached to handpiece 38 contacts tissue 44 being treated to ensure that radiation is always delivered in the same spot size as the handpiece is moved to different locations on tissue 44. It is also possible to employ a handpiece that delivers a collimated beam. This allows for a range of variation of working distance while still maintaining a selected beam size.

In experimental treatments in accordance with the present invention, laser 22 was arranged to deliver a spot having a diameter of about 3 mm. The pulse duration was about 2.0 ms. An average fluence of 5.5 J/cm$^2$ was used to treat facial wrinkles of volunteer patients. A total of eleven volunteer patients were treated.

Wrinkles were treated by applying single pulses at adjacent locations over the area without overlapping pulses. There was a high degree of patient satisfaction with the improvement of their appearance after an average of three treatments (one treatment about every three to five weeks). There was on average about a 52% improvement in wrinkles, the judgment of improvement being made by the patients themselves.

In establishing a suitable fluence for treatment for each patient, test pulses were delivered to a selected test area of that patient's skin, in a range of increasing fluences, until a fluence level was reached which produced observable, but mild, erythema. Each test pulse was fired on a different portion of the patient's skin. It was found that fluences higher than 12 J/cm$^2$ at a pulse length of 2 ms generally caused immediate blistering, even on light-skinned patients. Accordingly a fluence less than about 10 J/cm$^2$ in a pulse having a duration of about 2 ms or somewhat less is preferred. It should be noted here that this simple inflammation does not constitute a wound as that term is defined herein. Under no circumstances should the treatment parameters be sufficient to cause coagulation of blood in the vasculature.

Inflammation is a very specific process and is not synonymous with irritation. It is emphasized, however, that it is not necessarily the inflammation in itself that is responsible for the dermal ECM deposition and corresponding improvements of the inventive treatment. Rather, it is believed that it is the directed inflammatory process of the present invention which promotes the ECM growth, whether or not inflammation is clinically evident. Numerous inflammatory skin conditions, such as vasculitis, Sweet's syndrome and insect bites, occur without deposition of dermal ECM.

The experimental treatments were performed without resort to any skin cooling mechanisms such as contact cooling, cryogen spray cooling or the application of cooling gels to areas being treated. It is possible, however, that the method of the present invention may be made part of an integrated approach to the treatment of wrinkles by combining the above-described radiation therapy with application of agents such as alpha-hydroxy acids, retinoids and growth factors that can positively impact the healing response.

It should be noted, here, that the while above-described experimental treatments were conducted using the 532 nm wavelength of a frequency-doubled Nd:YAG this particular wavelength should not be construed as limiting the invention. By way of example using an appropriately wavelength selective resonator, a frequency doubled Nd:YAG laser can be arranged to deliver other wavelengths in the region between about 525 nm and 555 nm. These other wavelengths are about 531 nm, about 537 nm and about 539 nm which can be produced by frequency doubling fundamentally radiation at respectively about 1061 nm, about 1073 nm and about 1078 nm, the term about here meaning that the wavelengths are stated as rounded to the nearest nanometer. 532 nm radiation may also be generated by a frequency-doubled Nd:YV0$_4$ laser. The use of any other laser providing radiation in the preferred, 525 nm to 550 nm range is not precluded in the present invention, nor is the use of any source of non-coherent light delivering radiation in this preferred wavelength range.

It should also be noted that while single pulse delivery of radiation in experimental treatments is described, it is also possible to use continuous wave (CW) radiation and scan the radiation over tissue being treated. Scan speed (accordingly the dwell time of a beam in a particular area) can be selected, consistent with the beam-size and power in the CW beam, such that the dwell time of radiation at a point being treated (due to the time taken for a beam of finite size to pass that point) delivers the appropriate fluence as indicated above.

The present invention is described above in terms of a preferred and other embodiments. The invention is not limited, however, by the embodiments described and depicted herein. Rather, the invention is limited only by the claims appended hereto.

What is claimed is:

1. A method for treating wrinkles in human skin, comprising:

irradiating the skin with light having a wavelength between about 525 nanometers and 550 nanometers at a fluence level sufficient to promote a wound healing response promoting growth of dermal extracellular matrix in the upper dermal region in the skin but insufficient to cause a wound.

2. The method of claim 1, wherein said wavelength is about 532 nanometers.

3. The method of claim 1, wherein said fluence is less than about 10 J/cm².

4. The method of claim 1, wherein said light is delivered in the form of one or more pulses.

5. The method of claim 4, wherein said one or more pulses each have a duration of about 2 milliseconds or less.

6. The method of claim 1, wherein said light is delivered as CW radiation and is scanned over an area of skin being treated.

7. The method of claim 1, wherein said light is coherent light delivered by a laser.

8. The method of claim 1, wherein said light is incoherent light.

9. The method of claim 1, wherein said light is absorbed preferentially in a region of skin including a melanocyte layer of the epidermis and a region of superficial vasculature immediately below said melanocyte layer, thereby heating said region of skin to a temperature higher than normal body temperature but less than about 700° C., said heating promoting said would healing response.

10. A method for treating wrinkles in human skin, comprising:

irradiating the skin with light having a wavelength between about 525 nanometers and 550 nanometers such that a region of the skin including a melanocyte layer of the epidermis and a region of superficial vasculature immediately below said melanocyte layer are heated to a temperature higher than normal body temperature but less than about 70° C., said heating stimulating the production of dermal extracellular matrix in said region of the skin, said dermal extracellular matrix production reducing the depth of said wrinkles.

11. The method of claim 9, wherein said wavelength is about 532 nanometers.

12. The method of claim 9, wherein said fluence is less than about 10 J/cm².

13. The method of claim 9, wherein said light is delivered in the form of one or more individual pulses.

14. The method of claim 13, wherein said one or more pulses each have a duration of about 2 milliseconds or less.

15. The method of claim 9, wherein said light is delivered as CW radiation and is scanned over an area of skin being treated.

16. The method of claim 9, wherein said light is coherent light delivered by a laser.

17. The method of claim 9, wherein said light is incoherent light.

18. A method for treating wrinkles in human skin, comprising:

irradiating the skin with light having a wavelength selected such that it is preferentially absorbed in a region of the skin including a melanocyte layer of the epidermis and a region of superficial vasculature below said melanocyte layer, said light being delivered at a fluence sufficient that said preferential absorption thereof stimulates a wound healing response in said region of the skin without causing a wound, said wound healing response promoting growth of dermal extracellular matrix in said region of the skin, thereby reducing the depths of said wrinkles.

19. The method of claim 18, wherein preferential absorption heats said dermal region to a temperature higher than normal body temperature but less than about 70° C., said heating stimulating said would healing response.

* * * * *

UNITED STATES PATENT AND TRADEMARK OFFICE
CERTIFICATE OF CORRECTION

PATENT NO. : 6,808,532 B2 Page 1 of 1
APPLICATION NO. : 09/738523
DATED : October 26, 2004
INVENTOR(S) : Andersen et al.

It is certified that error appears in the above-identified patent and that said Letters Patent is hereby corrected as shown below:

At column 5, line 35: Please delete "700°C" and insert --70°C--.

Signed and Sealed this

Thirtieth Day of September, 2008

JON W. DUDAS
*Director of the United States Patent and Trademark Office*